United States Patent [19]

Shimamura et al.

[11] Patent Number: 5,744,179
[45] Date of Patent: Apr. 28, 1998

[54] LOW-PHOSPHORUS WHEY PROTEIN, MANUFACTURING METHOD THEREOF, LOW-PHOSPHORUS PURIFIED WHEY HYDROLYSATE AND MANUFACTURING METHOD THEREOF

[75] Inventors: Seiichi Shimamura; Yoshitaka Tamura; Teruhiko Mizota; Yasushi Kawaguchi; Yoko Nagasako; Hiroshi Ochi, all of Kanagawa, Japan

[73] Assignee: Morinaga Milk Industry Co., Ltd., Tokyo, Japan

[21] Appl. No.: 428,129

[22] PCT Filed: Nov. 26, 1993

[86] PCT No.: PCT/JP93/01729

§ 371 Date: Sep. 6, 1995

§ 102(e) Date: Sep. 6, 1995

[87] PCT Pub. No.: WO94/12053

PCT Pub. Date: Jun. 9, 1995

[30] Foreign Application Priority Data

Nov. 30, 1992 [JP] Japan .................. 4-320857
May 31, 1993 [JP] Japan .................. 5-129696

[51] Int. Cl.⁶ .................................. A23C 9/146
[52] U.S. Cl. .................. 426/41; 426/42; 426/271; 426/478; 426/491; 426/583; 426/656; 426/657

[58] Field of Search .................. 426/491, 478, 426/656, 657, 41, 42, 271, 583

[56] References Cited

U.S. PATENT DOCUMENTS

| | | | |
|---|---|---|---|
| 2,566,477 | 9/1951 | Abrahamczik | 426/41 |
| 3,974,294 | 8/1976 | Schwille et al. | 426/41 |
| 4,981,704 | 1/1991 | Thibault | 426/41 |

FOREIGN PATENT DOCUMENTS

| | | |
|---|---|---|
| 62-48695 | 3/1987 | Japan . |
| 2-117366 | 5/1990 | Japan . |
| 4-330252 | 11/1992 | Japan . |

*Primary Examiner*—Helen Pratt
*Attorney, Agent, or Firm*—Wenderoth, Lind & Ponack

[57] ABSTRACT

A whey protein having a phosphorus content reduced to below 0.15 mg per gram of protein, a manufacturing method thereof, a low-phosphorus hydrolysate highly purified having a low phosphorus content. The method comprises the steps of adjusting pH of the solution containing the whey protein to below 4, and contacting the solution with a cation exchange resin, sequentially contacting the solution with an anion exchange resin, thereby reducing the phosphorus content to below 0.15 mg per gram of protein, and the highly purified low-phosphorus whey protein hydrolysate of the present invention is available by hydrolyzing the above-mentioned low-phosphorus whey protein with proteases.

6 Claims, No Drawings

LOW-PHOSPHORUS WHEY PROTEIN, MANUFACTURING METHOD THEREOF, LOW-PHOSPHORUS PURIFIED WHEY HYDROLYSATE AND MANUFACTURING METHOD THEREOF

TECHNICAL FIELD

The present invention relates to a low-phosphorus whey protein, a manufacturing method thereof, a low-phosphorus purified whey hydrolysate and a manufacturing method thereof. More particularly, the present invention relates to a low-phosphorus whey protein useful for enriching various foods with nutritive value and protein, an easy and low-cost manufacturing method of the protein, a low-phosphorus purified whey hydrolysate which is useful as a substitutional substance of protein or amino acid for various food products and drug medicine and as a material for cosmetics, and a manufacturing method thereof.

In the following description, the term "protein (or a whey protein) hydrolysate" is defined as a mixture of peptide and free amino acid available from a hydrolysate of protein (or a whey protein); and the term "free amino acid content" is a weight percentage of the free amino acid content relative to the total amino acid content in the protein (or the whey protein) hydrolysate.

BACKGROUND ART

Whey is available as a by-product from manufacture of cheese or casein from cow's milk, and protein contained in the whey (hereinafter sometimes referred to as "whey protein") has a high nutritive value. A whey protein concentrate available by increasing the whey protein content has a further higher nutritive value as well as such excellent properties as a foaming propertiy, a high solubility and a good gel forming property. It is therefore applied in many food products such as dairy products, drink, meat products, sweets and cakes, and bread. Another use thereof is for enriching infant formula with protein.

More recently, utilization of peptide is attracting the general attention in various areas because of excellent nutritional and physiological properties including a high digestibility, a low antigenicity, a low osmic pressure, and a physiological activity as compared with a mixture of protein and amino acid of the same amino acid composition. Application of peptide is therefore studied, in addition to the conventional utilization in food products, widely in cosmetics and drug medicine. Enzymatic hydrolysate of whey protein is studied because of the suitability for industrial preparation in a large quantity of peptide.

Along with the expansion of uses, these whey protein and hydrolysates thereof are now required to have a unique quality in response to individual uses. When using whey protein or a hydrolysate thereof as a material for medical purposes, various restrictions are imposed on the chemical composition thereof, thus requiring a high-level purity.

It has recently been clarified that over-ingestion of phosporus from foods exerted an adverse effect on bone metabolism, and inhibition of the amount of ingested phosphorus is now attracting the general attention. In the medical area, for example, increase in the phosphorus concentration in blood of a patient subjected to dialytic treatment to remedy renal failure is now known to cause bone growth inhibition and other diseases, and as a result, it is desired to reduce the phosphorus content in foods ingested by such a patient. Since there is unavailable an effective therapeutic method without a side effect against hyperphosphatemia caused by various factors, there is a demand for low-phosphorus nutritive foods for patients thereof.

Because there is a demand for foods with a reduced phosphorus content as described above, achievement of a reduced phosphorus content in protein, an essential nutrient, is particularly an important task. For example, when aiming at improving the inorganic composition of whey protein, it is the usual practice to desalt whey protein. It is however very difficult to reduce the phosphorus content. It has actually been impossible to manufacture whey protein with a phosphorus content per gram of protein reduced to below 0.15 mg.

The known conventional methods for removing phosphorus contained in foods include: (a) a method of contacting skim milk having a pH adjusted to 5.2 to 8.0 with an anion exchanger (Japanese Patent Provisional Publication No. 60-256,342); (2) a method of adding calcium into whey to cause precipitation of free phosphoric acid in the form of calcium phosphate (Japanese Patent Provisional Publication No. 63-91,037); and (c) a method of contacting a liquid food with active alumina (Japanese Patent Provisional Publication No. 2-49,548).

Several of the present inventors developed a method for treating whey for the manufacture of low-phosphorus whey protein (Japanese Patent Provisional Publication No. 2-117,366; hereinafter referred to as the "prior application 1"). This method of the prior application 1 comprises the steps of concentrating a sweet whey to more than three times by the ultrafiltration method, adjusting pH to 3.0 to 4.5, contacting the concentrate with a cation exchanger to cause adsorption of protein, and causing elution of the adsorbed protein from the ion exchanger by means of a solution of a salt.

On the other hand, when using a protein hydrolysate in place of amine acid as a nitrogen component of an intravenous infusion, for example, antigenicity of the protein hydrolysate must previously be eliminated, and the composition of inorganic components including phosphorus is subjected to restrictions by the composition of the intravenous infusion as a whole. In order to prevent coloring of the liquid caused by amine carbonyl reaction during high-pressure sterilization or preservation in the manufacturing steps of the intravenous infusion, free amino acid, inorganic substances and a reducing sugar (e.g., lactose) should preferably be not in coexistence in the protein hydrolysate, and furthermore, there are imposed restrictions also on endotoxin because the infusion is administered into blood. In addition, the free amino acid content should naturally be the lowest possible because it takes the place of amino acid.

However, when using protein originating from cow's milk as a material for manufacturing whey protein hydrolysate, many ingredients to be adjusted or removed, such as inorganic matters, milk sugar and fat, are contained in the raw materials, and consequently, a highly purified whey protein hydrolysate satisfying all the above-mentioned conditions has never been available.

The conventionally known protein hydrolysates having properties related with the above-mentioned conditions and methods for manufacturing the hydrolysates include:

(d) a method for manufacturing a low-allergenized whey protein hydrolysate, which comprises the steps of enzyme-hydrolyzing a whey protein at a pH of 6 to 10 by means of a protein hydrolase, heating same to inactivate the enzyme, and obtaining the low-allergenized whey protein hydrolysate having a molecular weight distribution of up to 10,000, a main peak within a range of from 1,000 to 5,000, a free amino acid content of up to 20% (in weight percentage; this shall apply also hereafter unless otherwise specified), and en antigenicity of up to 1/10,000 that of β-lactoglobulin (Japanese Patent Provisional Publication No. 4-112.753); and (e) as peptide product comprising a peptide having a molecular weight of up to 6,000 daltons and as required an amino acid, and available through hydrolysis of a whey not containing an allergic substance or lactose, add a method for manufacturing a peptide product, which comprises the step of enzymatically hydrolyzing a whey protein residue obtained by dialfiltrating a concentrated whey (Japanese Patent Provisional Application No. 63-502,004).

Furthermore, several of the present inventors have previously applied for patent for a low molecular-weight peptide composition, which comprises a peptide having a molecular weight of up to 1,000 and not exhibiting antigenicity, a free amino acid content of up to 20%, and an aromatic amino acid content of up to 1.0% the total amino acid content; and s method for manufacturing a low molecular-weight peptide composition, comprising the steps of hydrolyzing a protein material with a protein hydrolase until until antigenicity is not observed and 90% of aromatic amino acid contained in the raw material protein become free amino acid, and collecting the peptide fraction by the gel filtration method (Japanese Patent Provisional Publication No. 2-138,991; hereinafter referred to as the "prior application 2"); a hydrolysate of milk protein which is a peptide mixture having a molecular weight of up to 1,000, and comprises free amino acid accounting for more than 90% of aromatic amino acid, not having antigenicity of milk protein (Japanese Patent Provisional Publication No. 4-26,604; hereinafter referred to as the "prior application 3"); a fraction of a hydrolysate of a milk protein which is a peptide mixture having a molecular weight of up to 1,000, daltons, and an aromatic amino acid content relative to the total amino acid content of up to 5%, and not having antigenicity of milk protein (Japanese Patent Provisional Publication No. 4-26,605; hereinafter referred to as the "prior application 4"); and an oligopeptide mixture available through hydrolysis of a milk protein having a purity of at least 70%, having a molecular weight distribution of up to 2,000 daltons, an antigen residual activity of up to $10^{-4}$ as measured by the ELISA (enzyme linked immuno-sorbent assay) method using antiwhey protein serum, and a free amino acid content of up to 5% relative to the total amino acid content; and a method for manufacturing an oligopeptide mixture, which comprises the steps of dissolving a whey protein having a purity of at least 70% by water to a concentration of up to 10%, adjusting pH of the resulting aqueous solution to a value of from 7.5 to 10, and enzyme-hydrolyzing same, inactivating the enzyme by heating or removing the enzyme through ultrafiltration (Japanese Patent Provisional Publication No. 4-248,959; hereinafter referred to as the "prior application 5").

In the above-mentioned methods (a), (b) and (c) among the conventional technologies for removing phosphorus in foods, however, it is impossible to remove phosphorus to a large extent from milk or a liquid food, and the limit phosphorus content per gram of protein is 40 mg, 10 mg and 6.4 mg, respectively. According to the above-mentioned method of the prior application 1, it is possible to reduce the phosphorus content to 0.44 mg per gram of protein for whey protein, but it is impossible to reduce the phosphorus content per gram of protein to a slight content of up to 0.15 mg.

In the conventional technologies, furthermore, while pH of the protein solution was adjusted prior to contacting the solution with a cation exchange resin or an anion exchange resin, it was usual that the lower limit of pH adjustment was limited by the occurrence of isoelectric precipitation of protein to be treated. When contacting the raw material protein solution with an $H^+$ type cation exchange resin, the solution becomes acidic under the effect of the decrease in pH, and specifically adjusting pH of the solution prior to contacting the solution with $H^+$ type cation exchange resin was not considered at all in any of the above-mentioned technologies, except for the prior application 1.

In the above-mentioned conventional technologies including (d) and (e) and the prior applications 2 to 5 covering the protein hydrolysates and the manufacturing methods thereof, some of the conditions such as the lactose content, the molecular weight distribution, the free amino acid content and antigenicity were examined, whereas it was impassible to reduce the phosphorus content per gram of protein to a trace amount of up to 0.15 mg. A protein hydrolysate having a high degree of purity for which all the items of the conditions such as the contents of inorganic substances, the lactose content, the molecular weight distribution, the free amino acid content, antigenicity, and the endotoxin content were considered has never been reported to date.

After filing applications for patent for the mentioned prior applications 1 to 5, the present inventors carried out extensive studies on a method for manufacturing a whey protein having a further reduced phosphorus content. As a result, it was found possible to remarkably reduce the phosphorus content of a whey protein by contacting the whey protein with a cation exchange resin and an anion exchange resin at a pH further lower than in the method of the prior application 1. They carried out further studies on hydrolysis of a whey protein having a low phosphorus content available by this method, and found it possible to obtain a highly refined protein hydrolysate having a phosphorus content further lower than that of the protein hydrolysates of the above-mentioned prior applications 2 to 5 and contents of inorganic substances, a lactose content, a molecular weight distribution, a free amino acid content, antigenicity and an endotoxin content all reduced. The present invention was thus completed.

Disclosure of Invention

The present invention provides a low-phosphorus whey protein having a phosphorus content of up to 0.15 mg per gram of protein.

The present invention provides also a method for manufacturing a low-phosphorus whey protein, which comprises the steps of adjusting pH of a solution containing a whey protein to a value of up to 4, and contacting the solution with an $H^+$ type cation exchange resin and sequentially contacting the solution with an anion exchange resin, thereby reducing the phosphorus content per gram of protein to below 0.15 mg.

The present invention provides a low-phosphorus purified whey protein hydrolysate having the following properties (1) to (6):

(1) the following inorganic substances are contained in the specified amounts per gram of protein:
sodium: up to 20 mg,
potassium: up to 20 mg,
magnesium: up to 0.057 mg,
phosphorus: up to 0.15 mg,
calcium: up to 0.227 mg,
chlorine: up to 0.568 mg;

(2) the lactose content is up to 0.5%;

(3) the fraction having a molecular weight of up to 1,200 is at least 90%;

(4) the free amino acid content is up to 6%;

(5) the value of antigenicity as measured by the ELISA (enzyme linked immuno-sorbent assay) method is up to $10^{-6}$ of that of β-lactoglobulin;

(6) the endotoxin content per gram of the dried material is up to 10 EU.

The present invention provides a method for manufacturing a low-phosphorus purified whey protein hydrolysate, which comprises the steps of adjusting pH of a solution containing a whey protein to a value of up to 4; contacting the solution with $H^+$ type cation exchange resin and and sequentially contacting with an $OH^-$ type anion exchange resin; adjusting pH of the solution to a value of at least 5 and up to 10; removing lactose from the solution through ultrafiltration; adding an enzyme complex comprising two or more enzymes including a protease derived from an animal and another protease isolated from a Bacillus-genus microorganism, or an enzyme complex comprising three or more enzymes including a protease derived from an animal, another protease isolated from a Bacillus-genus microorganism and further another protease to the solution, in order to cause enzyme-hydrolysis; heating the solution to inactivate enzymes and simultaneously to cause precipitation of non-reacting protein; and then removing fats and the precipitation from the solution through ultrafiltration.

In each of the above-mentioned manufacturing methods of the present invention, a preferred embodiment is to adjust pH of the solution containing the whey protein to a value of under 3.

According to the present invention, it is possible to very easily manufacture at a low cost a whey protein having a remarkably low phosphorus content that has never been achieved and to treat whey in an industrial scale in a large quantity.

There is provided also a whey protein hydrolysate having very low contents of phosphorus, lactose and endotoxin, and excellent in non-antigenicity and absorbency.

BEST MODE FOR CARRYING OUT THE INVENTION

First, the method for manufacturing a low-phosphorus whey protein of the present invention comprises the steps of adjusting pH of a solution containing a whey protein, and contacting the solution with an $H^+$ type cation exchange resin and sequentially contacting the solution with an anion exchange resin, thereby reducing the phosphorus content to below 0.15 mg per gram of protein.

Whey is a remaining liquid after removal of casein produced by adding an acid or rennet to whole milk or skim milk, and contains from about 0.3 to 0.7% protein.

The starting material used in the method for manufacturing a low-phosphorus whey protein of the present invention, which is a whey protein concentrate having a protein content of at least 70%, may be a commercially available product, or may be a concentrate available by separating protein from whey by a conventional method, and concentrating the thus separated protein to a protein content of at least 70%. This concentrate can be manufactured, for example, by a method of concentrating protein while eliminating low molecular weight substances through fractionation with ultrafiltration, a method of concentrating by adsorbing protein to a cation exchanger and an anion exchanger, and then causing elution thereof, or a method of collecting protein simultaneously with desalting and lactose-removal by means of a column filled with a gel filtration carrier. The phosphorus content in a whey protein concentrate varies with the manufacturing method: for currently commercially available protein concentrates, the phosphorus content is within a range of from 0.4 to 5.0 mg per gram of protein, This starting material is diluted to prepare a solution having a whey protein concentration of about 5 to 20%, and pH is adjusted to a value of up to 4, or more preferably, under 3 by adding an acid. Acids applicable for pH adjustment include hydrochloric acid, citric acid, lactic acid, acetic acid and sulfuric acid. Because pH of the solution containing the whey protein is near the neutral, the isoelectric point (pH of about 5) of protein is passed through. It is therefore possible to adjust pH to a prescribed value without causing solidification of the whey protein by previously determining the amount of added acid necessary for adjusting pH to a desired value, completing addition of that prescribed amount within a period of time of from several seconds to one minute, and promptly mixing and stirring the resultant mixture.

Then, the solution containing the whey protein, having a pH adjusted to a value of up to 4 is contacted first with an $H^+$ type cation exchange resin. The applied cation exchange resin may be any of strong acidic and weak acidic resins including such commercially available products as, for example, DIAION SK18 (trademark; made by Mitsubishi Chemical Industries, Ltd.), DUOLITE C-26 (trademark; made by Chemical Process Company), AMBERLITE IR-120B (trademark; made by Organo Company), and DOWEX MSC-1 (trademark; made by Dow Chemical Company).

After contact with this $H^+$ type cation exchange resin, pH of the solution containing the whey protein usually takes a value of about 1 to 2.5. When contact is caused with the $H^+$ type cation exchange resin near the neutral value of pH without adjusting pH of the solution containing the whey protein, as is clear from test examples described later, not only the effect of reducing the phosphorus content is not observed, but also the decrease in pH causes solidification by passage of the protein through the isoelectric point (near pH 5), thereby making it impossible to conduct a continuous ion exchange resin treatment.

Contact between the solution containing the whey protein having an adjusted pH and the cation exchange resin may be accomplished by any appropriate method such as the batch stirring method or the column continuation method. Any method permitting sufficient contact between the solution and the cation exchange resin may be adopted. When conducting the method of the present invention in an industrial scale, the column continuation method is preferable for the easy operation.

As to the mixing ratio of the solution containing the whey protein and the cation exchange resin, varying with the adsorbing ability of the ion exchange resin, the overall exchange capacity (equivalent) of the cation exchange resin must be larger than the total amount (equivalent) of cations of the solution containing the whey protein: it should preferably be two to five times as large from the point of view of resin utilization efficiency.

Temperature upon contact between the solution containing the whey protein and the cation exchange resin may be within a range of from 0° to 80° C. at which no thermal denaturation of the whey protein is caused, or should more preferably be within a range of from 0° to 10° C. with a view to preventing putrefaction caused by microorganisms. The contact time with the solution containing the whey protein may be appropriately selected by taking account of the temperature upon contact and the adopted manner of contact. In the batch stirring method, for example, contact is caused in a reaction vessel while conducting stirring and mixing or about 0.5 to 3 hours, whereas in the column continuation method, this step is accomplished at a velocity of SV=0.01 to 20 $h^{-1}$, or more preferably, SV=2 to 15 $h^{-1}$.

Then, the solution containing the whey protein after contact with the cation exchange resin is further contacted with an scion exchange resin. The anion exchange resin used here may be any of a strong basic and weak basic resins, and applicable ones include such commercially available products as DIAION PA318 (trademark; made by Mitsubishi Chemical Industries, Ltd.), DUOLITE A-118 (trademark; made by Chemical Process Company), AMBERLITE IRA-411 (trademark; made by Organo Company), and DOWEX MWA-1 (trademark; made by Dow Chemical Company). The opposite ion as the anion exchange resin may be any of $OH^-$ type and $Cl^-$ type. Preparation into an $OH^-$ type one permits desalting of the solution and reduces acidity through the increase in pH. When neutralizing the solution after treatment, therefore, it is possible to save the consumption of a neutralizer (alkali agent). The manner of bringing the anion exchange resin into contact, and conditions for the contact are the same as in the case of the cation exchange resin.

To recover solids of the residual solution in the resins, the resins may be washed by purified water.

The value of pH of the solution available through the ion exchange treatment is usually about 1 to 4 and may be neutralized by using as required a neutralizer (alkali agent) such as sodium hydroxide or potassium hydroxide. It is possible to manufacture a desalted and lactose-removed low-phosphorus whey protein by conducting fixed-volume flowing water diafiltration by means of an ultrafiltration membrane in a solution state of the resultant low-phosphorus whey protein. The solution containing the low-phosphorus whey protein thus obtained may be directly prepared into a product, or may as required be prepared into powder by concentrating and drying by a conventional method.

The thus obtained whey protein has much a very low phosphorus content as up to 0.15 mg per gram of protein, and is applicable as a material for foods with the use of excellent nutritional value, foaming property and emulsifying property. It is suitable also as a material for nutritive foods for a patient for whom ingestion of phosphorus is limited such as one suffering from hyper-phosphatemia: it is utilizable as a highly refined whey protein having a remarkably reduced phosphorus content which is most difficult to eliminate.

Now, the method for manufacturing a low-phosphorus refined whey protein hydrolysate of the present invention, which comprises the steps of adjusting pH of a solution containing a whey protein to a value of up to 4, contacting the solution with an $H^-$ type cation exchange resin and sequentially contacting the solution with an $OH^-$ type anion exchange resin; adjusting pH of the solution to a value of at least 5 and up to 9; removing lactose from the solution through ultrafiltration; enzyme-hydrolyzing the solution by adding an enzyme complex comprising two or more enzymes including a protease derived from an animal and another protease isolated from a Bacillus-genus microorganism, or an enzyme complex comprising three or more enzymes including a protease derived from an animal, another protease isolated from a Bacillus-genus microorganism, and further another pretease; inactivating the enzymes by heating; causing precipitation of non-reacting portion of the protein, and then ultrafiltering the resultant product, thereby removing the precipitate and fats.

The starting material used in the method for manufacturing a low-phosphorus refined whey protein hydrolysate of the present invention is the same whey protein concentrate as the starting material used in the method for manufacturing the above-mentioned low-phosphorus whey protein of the present invention.

This starting material is diluted to prepare a solution having a whey protein concentration of about 5 to 20%, and pH is adjusted to a value of up to 4, or more preferably, under 3 by adding an acid. Acids applicable for pH adjustment include hydrochloric acid, citric acid, lactic acid, acetic acid and sulfuric acid. Use of hydrochloric acid is preferable because it does not exert an adverse effect on flavor of the final product, and the $OH^-$ type anion exchange resin eliminates $Cl^-$ ions which do not finally remain. Because pH of the solution containing the whey protein is near the neutral, the isoelectric point (pH of about 5) of protein is passed through. It is therefore possible to adjust pH to a prescribed value without causing solidification of the whey protein by previously determining the amount of added acid necessary for adjusting pH to a desired value, completing addition of that prescribed amount within a period of time of from several seconds to one minute, and promptly mixing and stirring the resultant mixture.

Then, the solution containing the whey protein having a pH adjusted to a value of up to 4 is contacted first with an $H^+$ type cation exchange resin, and then with an $OH^-$ type anion exchange resin for desalting. The kind of the ion exchange resin selected, the manner of contacting the ion exchange resin, and the conditions for contact are the same as in the above-mentioned method for manufacturing the low-phosphorus whey protein of the present invention. In order to keep the contents of inorganic substances in the finally available whey protein hydrolysate, the solution can be desalted by using an opposite ion of the anion exchange resin prepared in the form of $OH^-$ type. Furthermore, since the increased pH reduces acidity, it is possible, when pH of the solution is made neutral or alkaline after the ion exchange treatment, to save the consumption of the neutralizer (alkali agent). To recover solids of the residual solution in the resins, the resins may be washed by purified water.

Because the desalted whey protein solution thus obtained has an acidic pH, a neutralizer (alkali agent) is added to adjust pH to a value of at least 5 and up to 10, or more preferably, to a value of at least 6 and up to 9. Neutralizers (alkali agents) applicable for adjustment of pH include sodium hydrochloride and potassium hydrochloride. This pH adjustment operation has an object to prevent corrosion by oxidation of, for example, manufacturing facilities, and prevent elution of inorganic ions from metallic portions of the manufacturing facilities. Another object is to cause pH of the whey protein solution to match with the optimum pH range of the enzyme used in the enzyme hydrolysis in the present invention. When there is no risk of corrosion by oxidation of manufacturing facilities, therefore, it is not necessary to conduct pH adjustment operation of the desalted whey protein solution immediately after the above-mentioned desalting operation with the aim of complying with the optimum pH range of enzyme, but is may appropriately be carried out before enzyme-hydrolysis operation. For example, when there is no corrosion by oxidation of manufacturing facilities, it is possible to adjust pH of the desalted and lactose-removed whey protein solution to the optimum pH range of enzyme used in the present invention, immediately before the enzyme-hydrolysis operation after the lactose removing operation, the next step, without adjusting pH immediately after the desalting operation.

Another possible embodiment comprises roughly adjusting pH of the above-mentioned desalted whey protein solution, immediately after the desalting operation, within a range permitting prevention of corrosion by oxidation of manufacturing facilities, and after conducting the next lactose removing operation, adjusting pH of the desalted and lactose-removed whey protein solution within the optimum pH range of the enzyme used in the present invention, immediately before the enzyme-hydrolysis operation.

Then, lactose contained in the desalted whey protein solution is removed by ultrafiltration. Ultrafiltration membranes having a fraction molecular weight within a range of from 2,000 to 10,000 are applicable, and any of the ultrafiltration methods common in this technical field is applicable. Applicable ultrafiltration modules include, for example, the flat membrane type, the tubular type, the spiral type, and the hollow fibre type. When taking account of the separating efficiency and economic merits, use of the tubular type or the hollow fibre type is preferable.

Because β-lactoglobulin and α-lactalbumin in the whey protein contained in the desalted whey protein solution have a molecular weight of about 18,000 and about 14,000, respectively, these whey proteins do not permeate through the ultrafiltration membrane upon ultrafiltration of the desalted whey protein solution, but lactose having a smaller molecular weight is discharged as a membrane permeating fraction. Furthermore, lactose can be eliminated almost completely by conducting fixed-volume flowing water diafiltration with purified water. Since the whey protein does not permeate the ultrafiltration membrane but is held within the membrane, the operation of fixed-volume flowing water diafiltration exerts no adverse effect on yield. Because ultrafiltration causes inorganic substances to be discharged on the membrane permeation liquid side, desalting effect is also available.

The whey protein concentration of this desalted and lactose-removed whey protein solution is adjusted to under 10%, and then an enzyme is added to the solution.

The enzyme used here is an enzyme complex comprising two or more enzymes including a protease derived from an animal and a protease isolated from a Bacillus-genus microorganism, or an enzyme complex comprising three or more enzymes including a protease derived from an animal, another protease isolated from a Bacillus-genus microorganism, and further another protease. Applicable professes originating from animals include trypsin, chymotrypsin, and pancreatin, all of which are commercially available (for example, "PTN 6.0S," a trademark; made by Novo Nordisk Company). Proteases isolated from Bacillus-genus microorganisms include PROTEASE N (trademark; made by Amano Seiyaku Company), BIO-PRASE (trademark; made by Nagase Seikagaku Kogyo Company), PROLEATHER (trademark; made by Amano Seiyaku Company), and ALCALASE (made by Novo Nordisk Company).

With a view to reducing antigenicity of the resultant whey protein hydrolysate, the object is well achieved With an enzume complex comprising a simple combination of a protease derived from an animal and a protease isolate from a Bacillus-genus microorganism. However, when a whey protein hydrolysate available by the use of an enzyme complex of such a combination is poor in flavor, It is possible to improve flavor by simultaneously using another protease. Such other proteases applicsble in this case include PAPAIN, BROMELINE (made by Amano Seiyaku Company), a protease isolated from an Aspergillus-genus microorganism, and a protease isolated from Penicillium-genus microorganism.

The amount of enzymes used should be within a range of from 3,800 to 20,000 activity units per gram of whey protein, and the enzyme complex is added by mixing or dividing.

Because the optimum value of pH of the enzyme used in the present invention is within a range of from neutral toward alkali side, the value of pH upon hydrolysis should be within a range of at least 5 and up to 10, or more preferably, at least 6 and up to 9.

There is no particular limitation on temperature conditions for hydrolysis based on enzymatic reaction: temperature may be selected within a practicable range including the optimum temperature range in which the enzyme action can manifest, and should be within a range of at least 30° C. and up to 70° C. in general, or more preferably, of at least 30° C. and up to 60° C., or further more preferably, of at least 50° C. and up to 60° C. Particularly, it is possible to prevent putrefaction of the whey protein solution during enzymatic reaction by keeping temperature within a range of at least 50° C. and up to 60° C.

The time required for enzymatic reaction may be determined in advance through a preliminary experiment. More specifically, the determination of time for enzymatic reaction is accomplished, for example, by sampling reaction liquid little by little at certain time intervals from the start of enzymatic reaction, subjecting the sampled reaction liquid to an arresting treatment of the enzymatic reaction and the ultrafiltration treatment of the present invention, drying the resultant filtrate by the conventional method into powder, determining, for this powder, the molecular weight distribution, the free amino acid content and antigenicity by the method described later, and using the enzymatic reaction time in the case where a powder of a desired composition is achieved as the enzymatic reaction time upon executing the present invention thereafter. For example, an enzymatic reaction time of from 8 to 36 hours is required for obtaining a whey protein hydrolysate having the following properties in the present invention:

(i) a fraction having a molecular weight of up to 1,200 accounting for at least 90%;

(ii) a free amino acid content of up to 6%;

(iii) an antigenicity, as measured by the enzyme linked immuno-sorbent assay, of $10^{-6}$ of antigenicity of β-lactoglobulin.

After the stage at which the whey protein hydrolysate has come to have the above-mentioned properties along with the progress of the enzymatic reaction, the enzyme is inactivated by heating. Inactivation of the enzyme may be accomplished by heating the reaction liquid at a temperature of at least 80° C. for more than six minutes. This heating causes generation of an undissolved product of about 20 (vol.) % when centrifugally separating the reaction liquid.

The whey protein hydrolysate solution after heating and inactivation of the enzyme is ultrafiltered to eliminate the undissolved product and fats for purification of the solution and for removal of endotoxin. The undissolved product, fats and endotoxin do not permeate the ultrafiltration membrane but remain on the membrane holding liquid side. It is therefore possible to purify the whey protein hydrolysate solution and remove endotoxin by collecting the liquid having permeated through the membrane. An ultrafiltration membrane having a fractional molecular weight of up to 5,000 is applicable and the commonly adopted method in this field of art may be applied for ultrafiltration. Applicable modules for ultrafiltration include, for example, the flat membrane type, the tubular type, the spiral type and the hollow fibre type. When considering the separating efficiency and economic merits, use of the tubular type or the hollow fibre type is preferable.

The recovery ratio of peptide which is a valuable solid in the original liquid can be improved by carrying out fixed-volume flowing water diafiltration with purified water.

The resultant liquid may directly be used as a product, or may as required by converted into a powder by concentrating and dried by the conventional methods.

The thus obtained low-phosphorus purified whey protein hydrolysate of the present invention has the following properties (1) to (6):

(1) containing the following inorganic ingredients in the amounts shown per gram of protein:
sodium: up to 20 mg,
potassium: up to 20 mg,
magnesium: up to 0.057 mg,
phosphorus: up to 0.15 mg,
calcium: up to 0.227 mg,
chlorine: up to 0.568 mg;

(2) a lactose content of up to 0.5%;

(3) a fraction, having a molecular weight of up to 1,200, of at least 90%;

(4) a free amine acid content of up to 6%;

(5) an antigenicity, as measured by the enzyme linked immuno-sorbent assay, of up to $10^{-6}$ of antigenicity of β-lactoglobulin;

(6) an amount of endotoxin of up to 10 EU per gram of dried product.

More specifically, while properties of the low-phosphorus purified whey protein hydrolysate of the present invention may, for example, be within the following ranges (a) to (f), the present invention is not limited to those ranges:

(a) contents of inorganic ingredients per gram of protein:
sodium: from 0.04 to 17 mg,
potassium: from 0.01 to 17 mg,
magnesium: from 0.03 to 0.05 mg,
phosphorus: from 0.11 to 0.13 mg,
calcium: from 0.15 to 0.20 mg,
chlorine: from 0.40 to 0.50 mg;

(b) a lactose content within a range of from 0.1 to 0.4%;

(c) a fraction having a molecular weight of up to 1,200 within a range from 90 to 94%;

(d) a free amine acid content of from 4 to 6%;

(e) an antigenicity, as measured by the enzyme linked immuno-sorbent assay, of up to $10^{-6}$ of antigenicity of β-lactoglobulin (detection limit of the ELISA method described later);

(f) an amount of endotoxin of from 2 to 8 EU per gram of dried product.

As shown in the above-mentioned properties (1) to (6), the low-phosphorus purified whey protein hydrolysate is suitably applicable as a nitrogen ingredient of an intravenous infusion, for example, in place of amino acid because of the low inorganic contents and because endotoxin and antigenicity are almost completely eliminated. It is possible, in this case, to prevent coloring of the liquid caused by the amino carbonyl reaction during high-pressure vapor sterilization in the manufacturing process of an intravenous infusion or during storage thereof, since the contents of free amino acid, inorganic ingredients and lactose are limited to low levels. The low-phosphorus purified whey protein hydrolysate is a mixture of peptide and free amino acid. Because of the low free amine acid content of up to 6%, an intravenous infusion using the low-phosphorus puriied whey protein hydrolysate as a nitrogen ingredient can be prepared into an infusion of a low osmotic pressure as compared with an intravenous infusion using an amino acid mixture of the same chemical composition as a nitrogen ingredient. In addition, since phosphorus the most difficult to remove among inorganic matters is remarkably reduced, it is applicable as a substitute for protein excellent in digestibility having a high degree of refining to be used as a material for a nutritional meal for a patient of a limited ingestion of phosphorus such as a patient suffering from hyperphosphatemia.

The low-phosphorus purified whey protein hydrolysate of the present invention was subjected to the following tests:

(1) Measurement of the Inorganic Matter Contents

The contents of sodium, potassium, magnesium, phosphorus and calcium were determined by the conventional method (edited by the Japan Society of Analytical Chemistry, Machine Analysis Practice Series, "ICP Emission Analysis Method," p. 225, Kyoritsu Shuppan, 1988) per gram of protein in a sample, together with the protein content in a sample measured by the conventional method. The chlorine content was measured by the potentiometric titration method (Japan Food Industry Association, edited by the Food Analysis Editing Committee, "Food Analysis Methods," 2nd ed., p. 368, Korin Publishing Company, 1984).

(2) Measurement of Lactose Content

The lactose content was measured by High Performance liquid chromatography (Journal of the Japan Food Industry Association, Vol. 27, No. 7, p. 36, 1980). Using Shodex DC613 (made by Showa Denko Company), elution was caused by means of an eluate having an acetonitrile:water ratio of 75:25 at an elution rate of 1.2 ml/minute. Detection was carried out by the post-label method [Bunseki Kagaku, Section E, Vol. 32, No. 6, p. E207, 1983] by means of a fluorescent detector (made by Shimazu Works; SHIMAZU RF530). The lactose content was calculated by the internal standard method (Japan Society of Analytical Chemistry, edited by Kanto Branch, "High Performance Liquid Chromatography Handbook," 277, Maruzen Company, 1985).

(3) Measurement of Molecular Weight Distribution

The molecular weight distribution was measured by High Performance liquid chromatography (N. Ui, et al., "High Performance Liquid Chromatography of Protein and Peptide," Kogaku, Additional Issue No. 102, p. 241, Kagaku Dojin Company, 1984). Elution was caused by means of a poly hydroxyethyl aspartamide (made by Poly LC Company) column, with 50 mM formic acid at an elution rate of 0.5 ml/minute. An RI detector (made by Shimazu Works) was used for detection, and a GPC analysis system (made by Shimazu Works) was used for data analysis.

(4) Measurement of Free Amino Acid Content

The content of each of the amino acids other than tryptophane, cysteine and methionine was determined by hydrolyzing a sample with 6N hydrochloric acid at 110° C. for 24 hours, alkaline-decomposing the sample, for tryptophane, with barium hydroxide at 110° C. for 22 hours, or hydrolyzing the sample, for cysteine and methionine, with 6N hydrochloric acid at 110° C. for 18 hours after a performic acid treatment, and decomposing same by an appropriate amino acid analyzer (made by Hitachi Seisakusho; Model 835). The free amino acid content was analyzed by means of an amino acid analyzer (made by Hitachi Seisakusho; Model 835) and was expressed in percentage of free amino acid relative to the total content of the individual amino acids as derived from the above-mentioned analysis of amino acid composition.

(5) Measurement of Antigenicity

Antigenicity was determined by the ELISA (enzyme linked immuno-sorbent assay) method as follows:

Antigenicity was measured by coating a 96-hole plate (made by Nunk Company) with β-lactoglobulin, then after washing, supplying a mixed solution of rabbit antiserum prepared through sensitization of β-lactoglobulin and a sample whey protein hydrolysate to the holes of the plate to cause a reaction, then after washing, causing a reaction of alkali-phosphatase label goat anti-rabbit IgG antibody (made by Zymed Laboratories), then after washing, adding p-nitrophenyl sodium phosphate which is an enzyme substrate, adding sodium phosphate, adding 5N sodium hydroxide after the lapse of 30 minutes to arrest the reaction, and measuring the resultant reaction product with a microplate reader (Journal of the Japan Infant Allergy Association, vol. 1, No. 2, p. 36, 1987).

(6) Measurement of Endotoxin Content

Endotoxin content was measured in accordance with the LIMULUS test (N. Niwa, Journal of the Japan Bacteriology Society, Vol. 30, p. 439, 1975), by means of a Limunlus HSII TESTWAKO (made by Wako Jun-Yaku Kogyo Company), to measure the gel forming time with a toxiometer ET201 (made by Wako Jun-Yaku Kogyo Company).

Now, the present invention is described further in detail by means of TESTs.

TEST 1

This test was carried out to investigate the effect of pH of a solution containing a whey protein on the decrease in the phosphorus content.

1) Preparation of Samples

A whey protein concentrate (made by Mirei Company, Germany; a protein content of 90% and a phosphorus content of 0.40 mg/gram of protein) was added to purified water, to adjust the concentration of the whey protein to 10%. Samples each weighing 600 g were prepared while adjusting pH by null (pH of 7.18; Samples 1 and 2), to 4.00 with 3N hydrochloric acid (Samples 3 to 6), to 3.00 (Sample 4) and to 2.00 (Sample 5).

2) Procedures

1. Method 1

Sample 1 was not contacted with an ion exchange resin, but directly subjected to measurement of the phosphorus content.

2. Method 2

Each of Samples 2 to 5 was passed through a column filled with an $H^+$ type cation exchange resin AMBERLITE IR-120B (made by Organo Company) in an amount of 50 ml at a velocity of SV=5 $h^1$ to contact with each other, and then passed through another column filled with an $OH^-$ type anion exchange resin AMBERLITE IR-411 (made by Organo Company) in an amount of 100 ml to contact with each other, thereby removing phosphorus in the sample.

3. Method 3

Sample 6 was treated in the same manner as in the above-mentioned method 2 except that the sample was not contacted with the $OH^-$ type anion exchange resin.

4. Measurement of Phosphorus Content

The phosphorus content was measured by the procedres as described above in the six Samples obtained by the above-mentioned three methods. The phosphorus content per gram of protein in the sample was calculated on the basis of the protein content in the sample as measured by the conventional method to test the status of phosphorus removal.

3) Results

The test gave results as shown in Table 1. As is clear from Table 1, in Samples 1 and 2 not subjected to pH adjustment, the ion exchange treatment reduces the phosphorus content from 0.40 mg only to 0.24 mg per gram of protein. In Samples 3 to 5 which were subjected to a cation exchange resin treatment and an anion exchange resin treatment after pH adjustment to below 4, in contrast, the phosphorus content was reduced to below 0.15 mg per gram of protein in all cases. Also in the case where pH of the solution containing the whey protein was adjusted to 4, the phosphorus content in Sample 6 brought into contact only with the $H^+$ type cation exchange resin was almost the same as that in Sample 2 subjected to an ion exchange resin treatment without adjusting pH.

To judge from these results, it is essential to adjust pH of the solution containing the whey protein to below 4, or more preferably, to below 3 prior to contacting the solution with the cation exchange resin and the anion exchange resin. Tests carried out by changing the kind of whey protein concentrate and the kind of resin gave almost the same results.

TABLE 1

| Sample No. | pH | Ion exchange treatment | Phosphorus content (mg/gram of protein) |
|---|---|---|---|
| 1 | 7.18* | Not treated | 0.393 |
| 2 | 7.18* | $H^+$, $OH^-$ | 0.241 |
| 3 | 4.00 | $H^+$, $OH^-$ | 0.114 |
| 4 | 3.00 | $H^+$, $OH^-$ | 0.107 |
| 5 | 2.00 | $H^+$, $OH^-$ | 0.093 |
| 6 | 4.00 | $H^+$ | 0.291 |

*Not adjusted

TEST 2

This test was carried out to investigate the effect of a change in the sequence of anion and cation exchange resins with which the solution is brought into contact on removal of phosphorus.

1) Preparation of Samples

A whey protein concentrate (made by Calpro Company; a protein content of 80% and a phosphorus content of 3.5 mg/gram of protein) was added to purified water to adjust the whey protein concentration to 10%, thereby preparing Samples 7 to 9 with a pH adjusted to 3.00 with 3N hydrochloric acid each in an amount of 100 g.

2) Procedures (1) Method 1

Sample 7 was not contacted with an ion exchange resin, but directly subjected to measurement of the phosphorus content.

(2) Method 2

Sample 8 was passed through a column filled with an $H^+$ type cation exchange resin AMBERLITE IR-120B (made by Organo Company) in an amount of 18.5 ml at a velocity of SV=5 $h^{-1}$ to contact with each other, and then passed through another column filled with a $Cl^-$-type anion exchange resin AMBERLITE IRA-411 (made by Organo Company) in an amount of 41.4 ml at a velocity of SV=5 $h^1$ to bring them into contact with each other, thereby removing phosphorus in the sample.

(3) Method 3

Sample 9 was treated in the same manner as in the method 2 except that the sample was first contacted with an anion exchange resin.

(4) Measurement of Phosphorus Content

The phosphorus content in the three samples obtained by the above-mentioned methods was measured in the same manner as in the TEST 1 to test the status of phosphorus removal.

3) Results

The results of this test are shown in Table 2. As is clear from Table 2, phosphorus cannot be removed unless the solution is first contacted with the cation exchange resin regarding the sequence of contact of the solution containing the whey protein with the cation exchange resin and the anion exchange resin. In the method of the present invention, therefore, it is essential to bring the solution containing the whey protein into contact first with the cation exchange resin, and then with the anion exchange resin. Tests carried out by changing the kind of whey protein concentrate and resin gave almost the same results.

TABLE 2

| Sample No. | pH | Ion exchange treatment | Phosphorus content (mg/gram of protein) |
|---|---|---|---|
| 7 | 3.00 | Not treated | 3.513 |
| 8 | 3.00 | $H^+$, $OH^-$ | 0.126 |
| 9 | 3.00 | $OH^-$, $H^+$ | 3.025 |

EXAMPLES

Now, the present invention is described further in detail by means of EXAMPLES. The present invention is not however limited by them.

In the following EXAMPLES, the contents of sodium, potassium, magnesium, phosphorus, calcium and chlorine are expressed in units of mg/gram of protein.

In the EXAMPLES of the present invention, the inorganic matter content, the lactose content, the molecular weight distribution, the free amino acid content, antigenicity and the endotoxin content were measured by the above-mentioned procedures of TESTS.

Example 1

A whey protein concentrate (made by Mirei Company, Germany; containing 90.3% protein, 5.1% sodium, 0.26% potassium, 0.33% magnesium, 0.39% phosphorus and 3.98% calcium) was added to purified water to adjust the concentration of the whey protein to 10%. Then, 3N hydrochloric acid in an amount of 134 ml was added to 1 kg this solution and pH was adjusted to 3.0. The solution was passed through a column filled with an $H^+$ type cation exchange resin AMBERLITE IR-120B (made by Organo Company) in an amount of 75 ml at SV=12.5 $h^1$ to contact with each other, and then passed through another column filled with a Cl- type anion exchange resin AMBERLITE IRA-411 (made by Organo Company) in an amount of 120 ml at SV=12.5 $h^1$ to contact with each other. Then, the columns filled with resin were washed by purified water to recover solids of the residual solution in them. The resultant solution of a pH of 2.11 containing a whey protein in an amount of about 3 kg was recovered, and freeze-dried by the conventional method, thereby obtaining a low-phosphorus whey protein powder in an amount of about 96 g.

The thus obtained powder was tested in accordance with the above-mentioned test methods: the inorganic composition comprised 0.3% sodium, 0.008% potassium, 0.0005% magnesium, 0.11% phosphorus and 0.008% calcium, suggesting that phosphorus was remarkably eliminated.

Example 2

A whey protein concentrate (made by Calpron Company; containing 83.0% protein, 1.45% sodium, 4.0% potassium, 0.65% magnesium, 3.39% calcium) was added to purified water to adjust the concentration of the whey protein to 10%. Then, 5N hydrochloric acid in an amount of 76.2 ml was added to 1 kg this solution and pH was adjusted to 2.8. The solution was passed through a column filled with an $H^+$ type cation exchange resin AMBERLITE IR-120B (made by Organo Company) in an amount of 100 ml at SV=2.5 $h^{-1}$ to contact with each other, and then passed through another column filled with a Cl- type anion exchange resin AMBERLITE IRA-411 (made by Organo Company) in an amount of 220 ml at SV=2.5 $h^1$ to contact with each other. Then, the columns filled with resins were washed by purified water to recover solids of the residual solution in them. The resultant solution of a pH of 1.96 containing a whey protein in an amount of about 3 kg was recovered, and freeze-dried by the conventional method, thereby obtaining a low-phosphorus whey protein powder in an amount of about 84 g.

The thus obtained powder was tested in accordance with the above-mentioned test methods: the inorganic composition comprised 0.038% sodium, 0.059% potassium, 0.0025% magnesium, 0.125% phosphorus and 0.0213% calcium, suggesting that phosphorus was remarkably eliminated.

Example 3

A whey protein concentrate (made by Mirei Company, Germany; containing 90.3% protein, 7.7% sodium, 0.60% potassium, 0.4% magnesium, 0.38% phosphorus, and 4.43% calcium) was added to purified water to adjust the concentration of the whey protein to 12.4%. Then 35% hydrochloric acid in an amount of 68 kg was added to 4.030 kg this solution and pH was adjusted to 3.05. The solution was passed through a column filled with an $H^+$ type cation exchange resin AMBERLITE IR-120B (made by Organo Company) in an amount of 350 l at SV=10 $h^1$ to contact with each other, and then passed through another column filled with an $OH^-$ type anion exchange resin AMBERLITE IRA-411 (made by Organo Company) in an amount of 700 l at SV=5 $h^1$ to contact with each other. Then, the columns filled with resins were washed by purified water to recover solids of the residual solution in them. The resultant solution of a pH of 3.50 containing a whey protein in an amount of about 6.825 kg was recovered, and freeze-dried by the conventional method, thereby obtaining a low-phosphorus whey protein powder in an amount of about 437 kg.

The thus obtained powder was tested in accordance with the above-mentioned test methods: the inorganic composition comprised 0.06% sodium, 0.03% potassium, 0.006% magnesium, 0.119% phosphorus and 0.023% calcium, suggesting that phosphorus was remarkably eliminated.

Example 4

A whey protein concentrate (made by Mirei Company, Germany; containing 90.3% protein, 5.1% sodium, 0.256% potassium, 0.331% magnesium, 0.392% phosphorus, 3.98% calcium and 1% lactose) was added to purified water to adjust the concentration of the whey protein to 12.4%. Then, 35% hydrochloric acid in an amount of 68 g was added to 4 kg this solution and pH was adjusted to 2.95. This solution was passed through a column filled with am $H^+$ type cation exchange resin AMBERLITE IR-120B (made by Organo Company) in an amount of 350 ml at SV=10 $h^1$ to contact with each other, and then passed through another column filled with an $OH^-$ type anion exchange resin AMBERLITE IRA-411 (made by Organo Company) in an amount of 700 ml at SV=5 $h^1$ to contact with each other. Then, the columns filled with resin were washed by purified water to recover solids of the residual solution in them. The resultant solution of a pH of 3.50 containing a whey protein in an amount of 6.83 kg was recovered.

A 10% sodium hydroxide solution in an amount of 0.15 kg was added to the recovered solution, and pH was adjusted to 6.9. Ultrafiltration was carried out through an ultrafiltration module SEP-1013 (made by Asahi Kasei Company; having a fractional molecular weight of 3,000) to discharge lactose and inorganic matters on the membrane permeating side, thereby obtaining s desalted and lactose-removed whey protein solution in an amount of 7.7 kg.

A 10% sodium hydroxide solution in an amount of 30 g was added to this desalted and lactose-removed whey protein solution, and pH was adjusted to 8.6. To this mixture, 4 g BIOPRASEsp-20 (made by Nagase Kagaku Kogyo Company), 2 g PTN6.0S (made by Novo Nordisk Company) and 4 g PROTEASE N "AMANO" (made by Amano Seiyaku Company) were added, and after decomposition at 50° C. for 14 hours, heated to 85° C. for ten minutes to inactivate the enzymes.

Then, this solution was subjected to an ultrafiltration through an ultrafiltration module SEP-1013 (made by Asahi Kasei Company; a fractional molecular weight of 3,000), and undissolved product remaining on the membrane was removed. The resultant filtrate was concentrated, and spray-dried by the conventional method, thereby obtaining about 256 g spray-dried product of a low-phosphorus refined whey protein hydrolysate.

The thus obtained powder was tested in accordance with the above-mentioned test methods: the inorganic composition comprised 15.2% sodium, 0.22% potassium, 0.04% magnesium, 0.12% phosphorus and 0.19% calcium, with 0.48% chlorine, a lactose content of 0.26%, a fraction having a molecular weight of up to 1,200 accounting for 92.4%, a free amino acid content of 5.4%, an antigenicity of up to $10^{-6}$ of that of β-lactoglobulin, and endotoxin of 5.15 EU/g per gram of dried whey protein hydrolysate.

Industrial Applicability

The low-phosphorus whey protein of the present invention is useful for increasing nutritive value and enriching protein of various food products.

The low-phosphorus purified whey protein of the present invention, of which the phosphorus content is kept at a very low level, is useful in food manufacturing and medical areas as a protein nutritive source to be orally or directly administered to the stomach of the intestine for a patient suffering from renal failure or hyper-phosphatemia who is required to limit ingestion of phosphorus. It is also excellent in non-antigenicity and absorbency and is therefore applicable as a protein nutritive source to be orally or directly administered to the stomach or the intestine for patients suffering from allergy, decreased physical fitness, gut immunity disease, allergic diarrhea, infants, and those before and after operation. Because of the very low contents of inorganic matters, lactose and endotoxin, it is applicable as a nitrogen source for an intravenous infusion or a peritoneum dialysis liquid.

We claim:

1. A low-phosphorus whey protein comprising a phosphorus content of up to 0.15 mg per gram of protein.

2. A method for manufacturing a low-phosphorus whey protein, which comprises the steps of:
   (a) adjusting pH of a solution containing a whey protein to below 4;
   (b) contacting the solution obtained by step (a) with an $H^+$ type cation exchange resin; and
   (c) sequentially contacting the solution obtained by step (b) with an anion exchange resin to reduce the phosphorus content per gram of protein to below 0.15 mg.

3. The method according to claim 2, wherein in step (c), the pH of the solution is adjusted to below 3.

4. A low-phosphorus purified whey protein hydrolysate having the following properties (1) to (6):
   (1) containing inorganic matters in the following amounts per gram of protein:
       sodium: up to 20 mg,
       potassium: up to 20 mg,
       magnesium: up to 0.057 mg,
       phosphorus: up to 0.15 mg,
       calcium: up to 0.227 mg, and
       chlorine: up to 0.568 mg;
   (2) a lactose content of up to 0.5% in weight;
   (3) a fraction having a molecular weight of up to 1,200 at least 90% in weight;
   (4) a free amino acid content of up to 6% in weight;
   (5) an antigenicity, as measured by the enzyme linked immuno-sorbent assay, of up to $10^{-6}$ of antigenicity of β-lactoglobulin; and
   (6) an endotoxin content of up to 10 EU per gram of dried product.

5. A method for manufacturing a low-phosphorus purified whey protein hydrolysate as claimed in claim 4, which comprises the steps of:
   (a) adjusting pH of a solution containing a whey protein to below 4;
   (b) contacting the solution obtained by step (a) with an $H^+$ type cation exchange resin;
   (c) sequentially contacting the solution obtained by step (b) with an $OH^-$ type anion exchange resin;
   (d) adjusting pH of the solution obtained by step (c) to at least 5 and up to 10;
   (e) removing lactose from the solution obtained by step (d) through ultrafiltration;
   (f) adding an enzyme complex comprising two or more enzymes including a protease derived from an animal and another protease isolated from a Bacillus-genus microorganism, or an enzyme complex comprising three or more enzymes including a protease derived from an animal, another protease isolated from a Bacillus-genus microorganism and further another protease to the solution obtained by step (e) in order to conduct enzymatic hydrolysis;
   (g) heating the solution obtained by step (f) to inactivate enzymes and simultaneously causing precipitation of non-reacting protein; and
   (h) removing fats and all precipitation from the solution obtained by step (g) through ultrafiltration.

6. The method according to claim 5, wherein in step (c), the pH of the solution is adjusted to below 3.

* * * * *